(12) United States Patent
Kim et al.

(10) Patent No.: US 9,618,468 B2
(45) Date of Patent: Apr. 11, 2017

(54) METHOD FOR MEASURING ELECTRICAL CONDUCTIVITY AND ELECTRICAL CONDUCTIVITY MEASURING SYSTEM USING THE SAME

(71) Applicants: KOREA ATOMIC ENERGY RESEARCH INSTITUTE, Daejeon (KR); KOREA HYDRO & NUCLEAR POWER CO., LTD., Gyeongsangbuk-Do (KR)

(72) Inventors: Jong Yun Kim, Daejeon (KR); Yong Suk Choi, Daejeon (KR); Sang Eun Bae, Sejong-Si (KR); Jei Won Yeon, Daejeon (KR); Kyuseok Song, Daejeon (KR)

(73) Assignees: KOREA HYDRO & NUCLEAR POWER CO., LTD., Gyeongsangbuk-Do (KR); KOREA ATOMIC ENERGY RESEARCH INSTITUTE, Daejeon (KR)

(*) Notice: Subject to any disclaimer, the term of this patent is extended or adjusted under 35 U.S.C. 154(b) by 639 days.

(21) Appl. No.: 14/062,822

(22) Filed: Oct. 24, 2013

(65) Prior Publication Data
US 2014/0132288 A1 May 15, 2014

(30) Foreign Application Priority Data
Nov. 13, 2012 (KR) .......................... 10-2012-0128352

(51) Int. Cl.
*G01N 27/06* (2006.01)
(52) U.S. Cl.
CPC .................................. *G01N 27/06* (2013.01)

(58) Field of Classification Search
CPC ............................... G01N 27/06; G01N 27/60
(Continued)

(56) References Cited

U.S. PATENT DOCUMENTS

| 4,119,909 A | 10/1978 | DeBerry |
| 5,334,940 A * | 8/1994 | Blades .................. G01R 27/22 324/439 |

(Continued)

FOREIGN PATENT DOCUMENTS

| JP | 59-162443 | 9/1984 |
| JP | 60-97247 | 5/1985 |

(Continued)

OTHER PUBLICATIONS

Notice of Allowance issued in Korean Patent Application No. 10-2012-0128352, dated Jun. 9, 2014, 2 pages.

*Primary Examiner* — Jermele M Hollington
*Assistant Examiner* — Zannatul Ferdous
(74) *Attorney, Agent, or Firm* — Morrison & Foerster LLP

(57) ABSTRACT

The present disclosure relates to a method for measuring electrical conductivity and a system for measuring electrical conductivity using the same. The method includes obtaining a cell constant of a conductance cell using a conductivity standard solution, pouring a solution desired to be measured in the conductance cell, and applying predetermined direct current (DC) voltages to electrodes, disposed in the conductance cell, in a manner of changing the predetermined DC voltages in stages at each preset time (t), obtaining resistance of the solution, as a slope, from a linear relationship between the voltage and a peak current, measured for each voltage, and calculating electrical conductivity of the solution using the cell constant and the resistance of the solution.

12 Claims, 20 Drawing Sheets

(58) Field of Classification Search
USPC .................................................. 324/693, 453
See application file for complete search history.

(56) References Cited

U.S. PATENT DOCUMENTS

| | | |
|---|---|---|
| 5,441,049 A | 8/1995 | Masano |
| 5,448,178 A | 9/1995 | Chen et al. |
| 5,708,363 A * | 1/1998 | Yates .................... G01R 27/22 |
| | | 324/442 |
| 2007/0024287 A1* | 2/2007 | Graves .................. G01N 27/06 |
| | | 324/453 |

FOREIGN PATENT DOCUMENTS

| | | |
|---|---|---|
| JP | 7-198643 | 8/1995 |
| JP | 7-209237 | 8/1995 |
| JP | 09-138207 | 5/1997 |
| JP | 10-197469 | 7/1998 |
| JP | 2000-74865 | 3/2000 |
| JP | 2002-330752 | 11/2002 |

* cited by examiner

METHOD FOR MEASURING ELECTRICAL CONDUCTIVITY AND ELECTRICAL CONDUCTIVITY MEASURING SYSTEM USING THE SAME

CROSS REFERENCE TO RELATED APPLICATION

Pursuant to 35 U.S.C. §119(a), this application claims the benefit of earlier filing date and right of priority to Korean Application No. 10-2012-0128352, filed on Nov. 13, 2012, the contents of which is incorporated by reference herein in its entirety.

BACKGROUND OF THE DISCLOSURE

1. Field of the Disclosure

This specification relates to a method for measuring electrical conductivity and a system for measuring electrical conductivity using the same.

2. Background of the Disclosure

Electrical conductivity is a material's ability to conduct an electric current when an electric field is applied thereto. The electrical conductivity is a quantity to show how each to conduct electricity. The electrical conductivity is one of unique properties of a solution, and is very important in the aspects of providing useful information on a chemical structure of the solute on the total concentration of the ionic species in solution and transport properties such as ionic mobility, diffusivity, viscosity, etc.

Methods for measuring electrical conductivity of a solution are generally divided into a method using a direct current (DC) and a method using an alternating current (AC). The method using the DC has been known as being generally used for a solution with high electrical conductivity. However, the method using the DC has a disadvantage in that a measurement error may be likely to be generated due to polarization on a surface of an electrode. Accordingly, the method using the AC is mostly used for measuring electrical conductivity in recent years.

On the other hand, the method using the AC is capable of reducing the polarization phenomenon on the surface of the electrode, but may be easily affected by ambient electromagnetic disturbance, and be difficult to be analyzed accurately in the field processes where there may be many electronic devices.

SUMMARY OF THE DISCLOSURE

Therefore, an aspect of the detailed description is to provide a method for measuring electrical conductivity capable of measuring electrical conductivity of a solution more accurately, and a system for measuring electrical conductivity using the same.

To achieve these and other advantages and in accordance with the purpose of this specification, as embodied and broadly described herein, there is provided a method for measuring electrical resistance and calculating electrical conductivity including obtaining a cell constant of a conductance cell using a conductivity standard solution, pouring a solution desired to be measured in the conductance cell, and applying predetermined direct current (DC) voltages to electrodes, disposed in the conductance cell, in a manner of changing the predetermined DC voltages in stages at each preset time (t), obtaining resistance of the solution, as a slope, from a linear relationship between the applied or measured voltage and a peak current, measured for each voltage, and calculating electrical conductivity of the solution using the cell constant and the resistance of the solution.

In accordance with one aspect of the present disclosure, the applying by changing the voltages in stages may be a step of applying the voltages by increasing or decreasing the voltages in stages at each preset time.

In accordance with another aspect of the present disclosure, the preset time may be shorter than a time at which polarization begins to occur on a surface of the electrode.

The preset time may be a time converged on 0 (t→0) to prevent the polarization on the surface of the electrode.

In accordance with another aspect of the present disclosure, the peak current may be a current measured at the moment when the predetermined DC voltage is applied.

In accordance with another aspect of the present disclosure, the obtaining of the cell constant may include applying the predetermined DC voltages to the electrodes by changing the voltages in stages at each preset time (T), and obtaining the resistance of the conductivity standard solution, as the slope, from the linear relationship between the voltage and the peak current measured for each voltage.

The applying by changing the voltages in stages, in the step of obtaining the cell constant, may be a step of applying the voltages by increasing or decreasing the voltages in stages at each preset time.

The preset time may be shorter than a time at which polarization begins to occur on a surface of the electrode.

The preset time may be a time converged on 0 (T→0) to prevent the polarization on the surface of the electrode.

To achieve these and other advantages and in accordance with the purpose of this specification, as embodied and broadly described herein, there is provided a system for measuring electrical conductivity including a conductance cell having electrodes, the conductance cell having an unique cell constant, a voltage applying unit that is configured to apply predetermined direct current (DC) voltages to the electrodes in a manner of changing the voltages in stages at each preset time, a current measuring unit that is configured to measure a peak current for each voltage, and a controller that is configured to obtain resistance of the solution, as a slope, from a linear relationship between the voltage and the peak current, and calculate electrical conductivity of the solution using the cell constant and the resistance of the solution.

In accordance with one aspect of the present disclosure, the voltage applying unit may be configured to increase or decrease the voltages in stages at each time, which is shorter than a time when polarization begins to occur on a surface of the electrode.

In accordance with another aspect of the present disclosure, the current measuring unit may be configured to measure a current at the moment when the predetermined DC voltage is applied.

Further scope of applicability of the present application will become more apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from the detailed description.

BRIEF DESCRIPTION OF THE DRAWINGS

The accompanying drawings, which are included to provide a further understanding of the disclosure and are incorporated in and constitute a part of this specification, illustrate exemplary embodiments and together with the description serve to explain the principles of the disclosure.

In the drawings.

DETAILED DESCRIPTION OF THE DISCLOSURE

Description will now be given in detail of a method for measuring electrical conductivity and a system for measuring electrical conductivity using the same according to the exemplary embodiments, with reference to the accompanying drawings.

For the sake of brief description with reference to the drawings, the same or equivalent components will be provided with the same or like reference numbers, and description thereof will not be repeated. The expression in the singular form in this specification will cover the expression in the plural form unless otherwise indicated obviously from the context.

Figure 1:
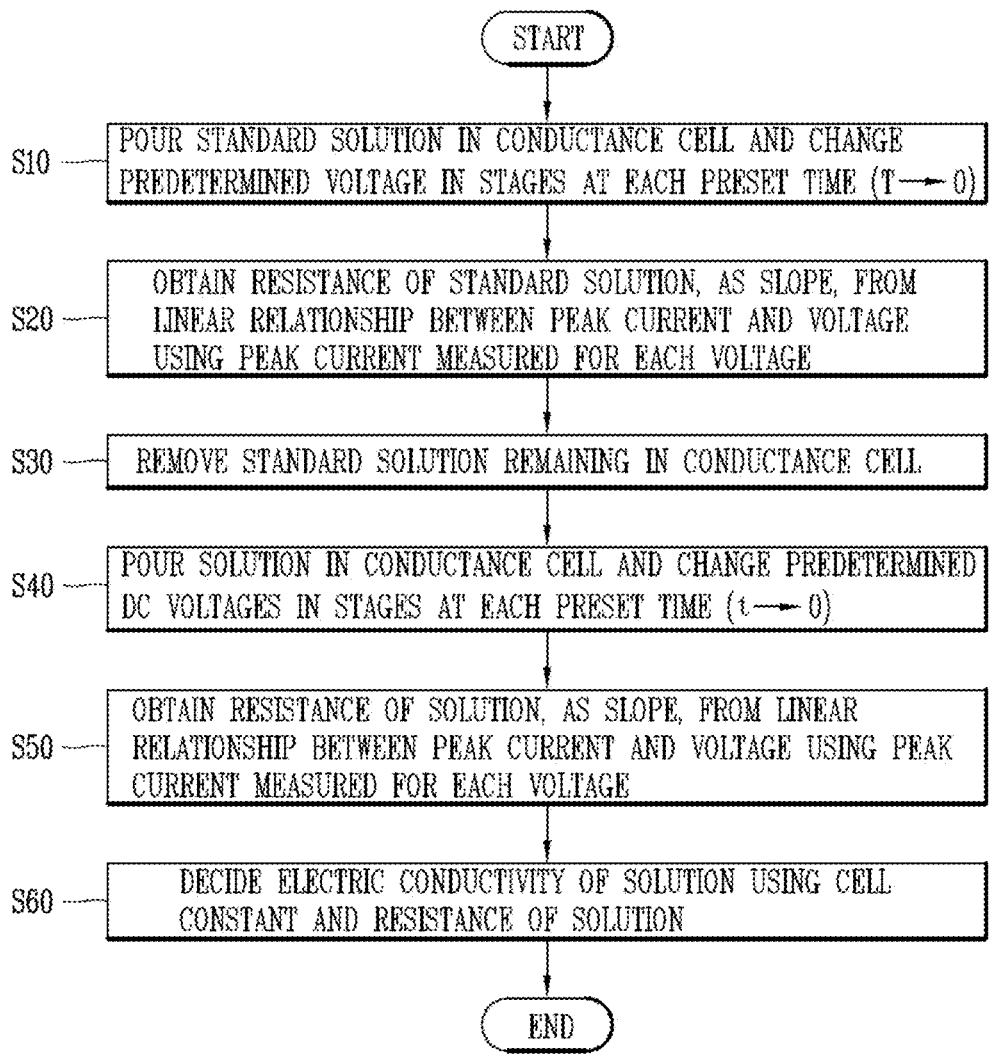
FIG. 1 is a flowchart illustrating a method for measuring electrical conductivity in accordance with one exemplary embodiment of the present disclosure.
Figure 2:
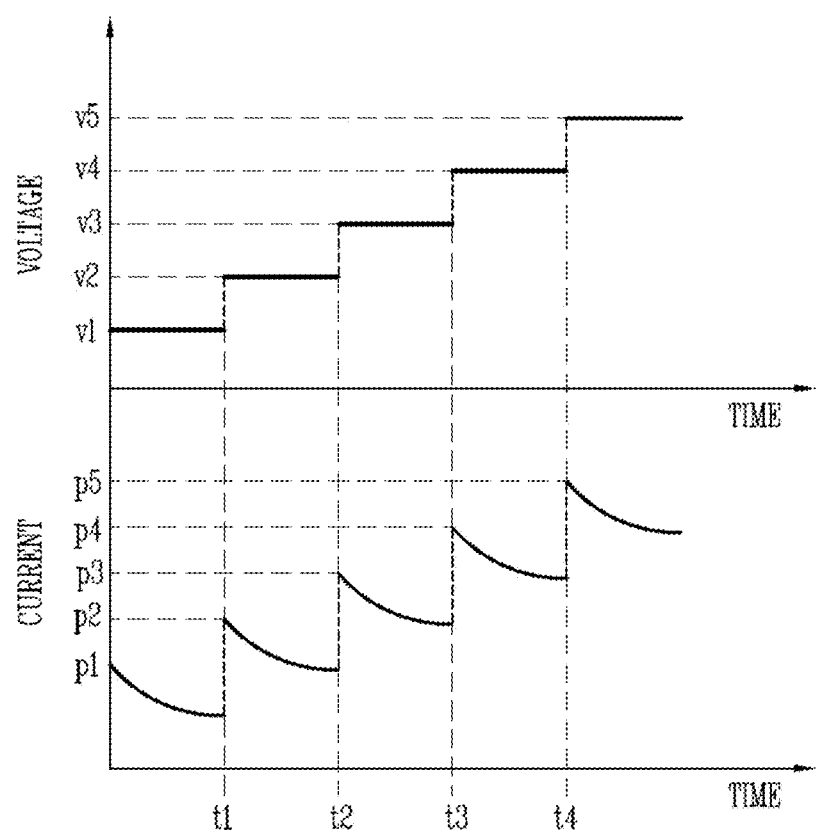
FIGS. 2 and 3 are conceptual views illustrating a method for obtaining resistance of a solution in a manner of increasing DC voltages in stages and using peak currents measured for each voltage.
Figure 3:
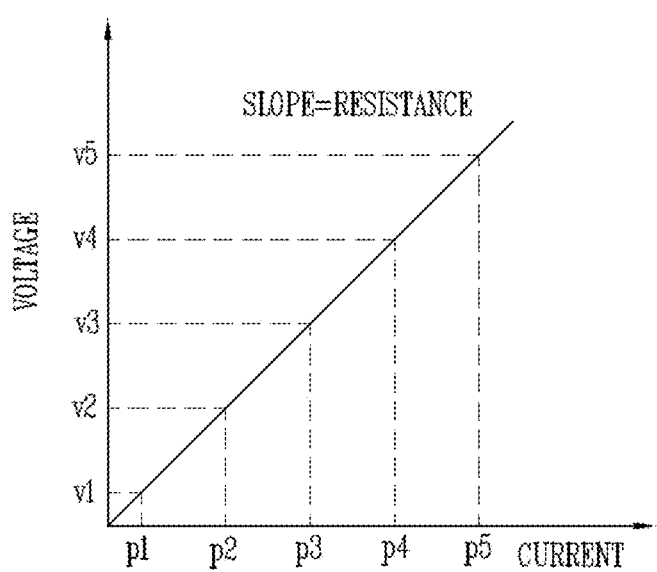

FIG. 1 is a flowchart illustrating a method for measuring electrical conductivity in accordance with one exemplary embodiment of the present disclosure. FIGS. 2 and 3 are conceptual views illustrating a method for obtaining resistance of a solution in a manner of increasing DC voltages in stages and using peak currents measured for the respective voltages. The method illustrated in FIGS. 2 and 3 may be applied to a method for measuring resistance of a conductivity standard solution and a method for measuring resistance of a solution desired to be measured.

To measure electrical conductivity of a solution 10 (see FIG. 4), the solution 10 may be poured in a conductance cell 110 (see FIG. 4) which includes a pair of conductive electrodes 111 (see FIG. 4), and a resistance value may be obtained through an experiment. And, the electrical conductivity may be calculated (measured) based on the obtained resistance value. The electrical conductivity X of the solution 10 may be calculated by dividing a distance L by a value $(A \times R)$, which is obtained by multiplying a surface area A of the electrodes 111 and a resistance value R of the solution together $[X=L/(A \times R)]$.

Therefore, to calculate the electrical conductivity X based on resistance, a cell constant C, which is a unique constant of the conductance cell 110, decided by the surface area A of the electrodes 111 and the distance L between the electrodes 111 $(C=L/A)$. However, since it is rarely possible to correctly measure the cell constant only by the experiment, the cell constant may be obtained by measuring a resistance value, which is generated when a conductivity standard solution of which specific conductance is correctly known is put into the conductance cell 110.

In order to obtain the cell constant using the conductivity standard solution, the conductivity standard solution may be poured into the conductance cell 110, and DC voltages may be changed in stages (step by step) at each preset time T (S10). The preset time may indicate a time when a predetermined DC voltage is applied.

FIG. 2 exemplarily illustrates that voltages v1, v2, v3, v4 and v5 are increasing in stages (in a form of steps) at each preset time. The voltages may also be decreasing step by step at each preset time, or arbitrary different voltages may be applied in an instantaneous manner.

Afterwards, peak currents may be measured for the respective voltages. As illustrated in FIG. 2, the current may gradually decrease with drawing a curve due to polarization, which occurs on a surface of the electrode 111 from the time point when the voltage is applied. Hence, if peak currents p1, p2, p3 and p4 prior to the occurrence of the polarization are measured, a measurement error due to the polarization may be prevented. This may allow for obtaining data which is the basis for calculating a more correct cell constant.

Here, the preset time at which a predetermined DC voltage is applied may preferably be set to a time, which is shorter than a time that the polarization begins to occur on the surface of the electrode 111 disposed in the conductance cell 110. The polarization may occur as soon as a voltage being applied. Therefore, the preset time, namely, T may preferably be set to a time, which is converged on 0, so as to prevent the polarization on the surface of the electrode 111.

That is, data of a voltage and a corresponding peak current may be obtained in a manner of instantaneously applying a first voltage, measuring a first current (namely, a first peak current) corresponding to the first voltage, instantaneously applying a second voltage higher than the first voltage, and measuring a second current (namely, a second peak current) corresponding to the second voltage.

Next, as illustrated in FIG. 3, a resistance value of the conductivity standard solution, as a slope, may be obtained from a linear relationship between the peak current and the voltage (S20). Accordingly, the cell constant may be calculated based on the resistance.

When the cell constant is decided, the conductivity standard solution contained in the conductance cell 110 may be removed, and a solution 10 desired to be measured may be poured in the conductance cell 110 (S30). Here, a washing process using distilled water or the like may preferably be executed to completely remove the remaining conductivity standard solution from the conductance cell 110.

Afterwards, as aforementioned, DC voltages may be changed step by step at each preset time t (S40), and a resistance value of the solution 10 as the slope may be obtained from a linear relationship between the peak current and the voltage using the peak currents measured for the respective voltages (S50). The preset time may indicate a time when the predetermined DC voltage is applied For example, as illustrated in FIG. 2, the voltages v1, v2, v3, v4 and v5 may gradually be increasing at each preset time t1, t2, t3, t4 and t5, and corresponding peak currents p1, p2, p3, p4 and p5 may be measured. On the contrary, the voltages may gradually be decreasing at each preset time, and corresponding peak currents may be measured. Since the resistance is represented as a linear slope in the graph showing voltages with respect to currents, the resistance may be easily obtained by applying two voltages with different magnitudes and measuring two peak currents for the two voltages. It may be, of course, obvious that more accurate resistance can be obtained based on more data if the number of applying a voltage increases.

As illustrated in FIG. 2, the current may gradually be decreasing with drawing a curve due to the polarization, which occurs on the surface of the electrode 11 at the time point when the voltage is applied. If the peak current, which is generated when the voltage prior to the occurrence of the polarization is applied, is measured, a measurement error due to the polarization may be prevented. This may allow for obtaining the resistance, which is the basis for measuring more correct electrical conductivity of the solution 10.

Here, the preset time for changing the voltage may preferably be set to a time, which is shorter than a time when the polarization begins to occur on the surface of the electrode 111 disposed in the conductance cell 110. The polarization may occur as soon as a voltage being applied. Therefore, the preset time, namely, T may preferably be set to a time, which is converged on 0, so as to prevent the polarization on the surface of the electrode 111. The preset time may be a time converged on 0, for example, a short time in a unit of millisecond, microsecond, or nanosecond.

That is, data of a voltage and a corresponding peak current may be obtained in a manner of instantaneously applying a first voltage, measuring a first current (namely, a first peak current) corresponding to the first voltage, instantaneously applying a second voltage higher than the first voltage, and measuring a second current (namely, a second peak current) corresponding to the second voltage.

Afterwards, a resistance value of the solution 10, which is slope, may be obtained from the linear relationship between the voltage and the peak current. As a result, the electrical conductivity of the solution 10 may be calculated based on the resistance value of the solution 10 and the cell constant, which has been obtained using the conductivity standard solution (S60).

Figure 4:
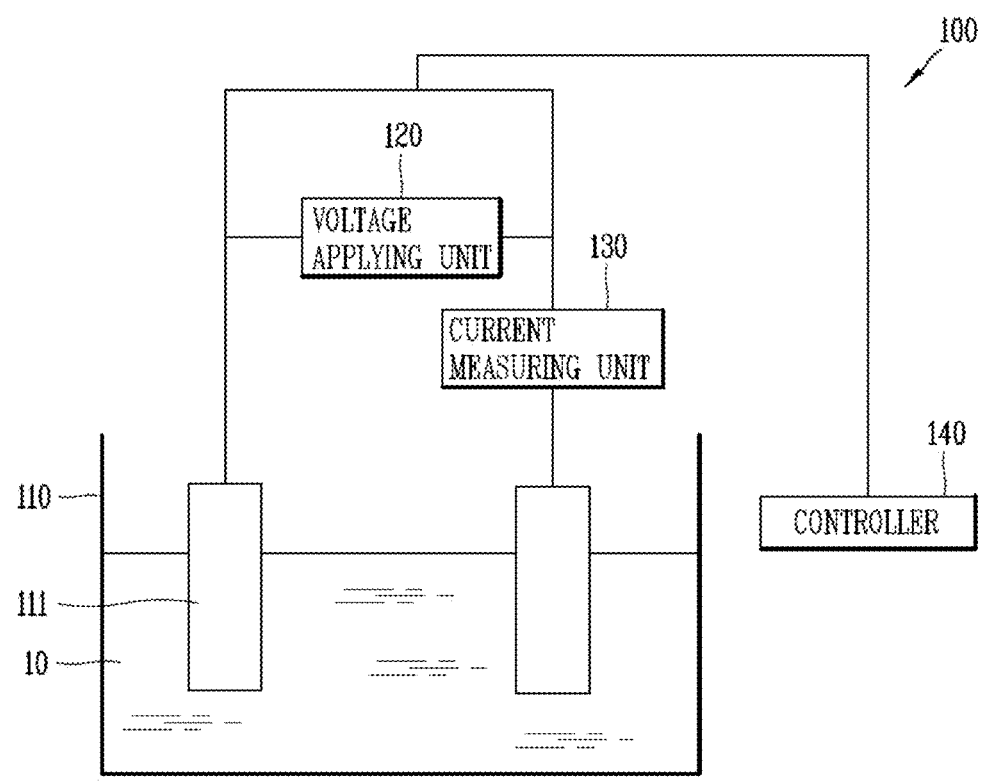
FIG. 4 is a conceptual view illustrating one exemplary embodiment of a system for measuring electrical conductivity in accordance with the present disclosure.
Figure 5A:
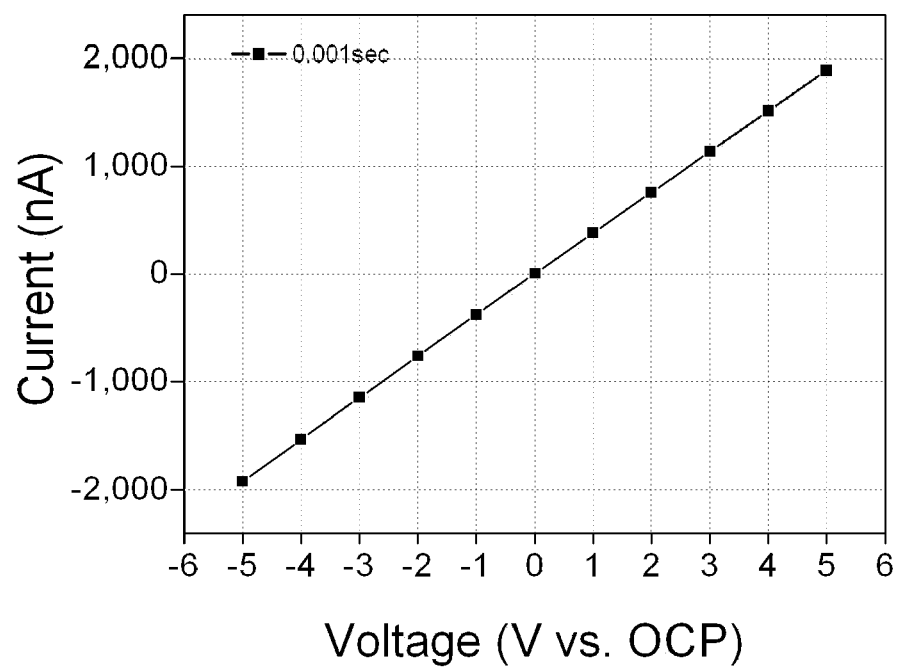
FIGS. 5A to 5F are graphs each illustrating applied voltages and resulting currents in 0.001 M of KCl conductivity standard solution based on a voltage application time.
Figure 5B:
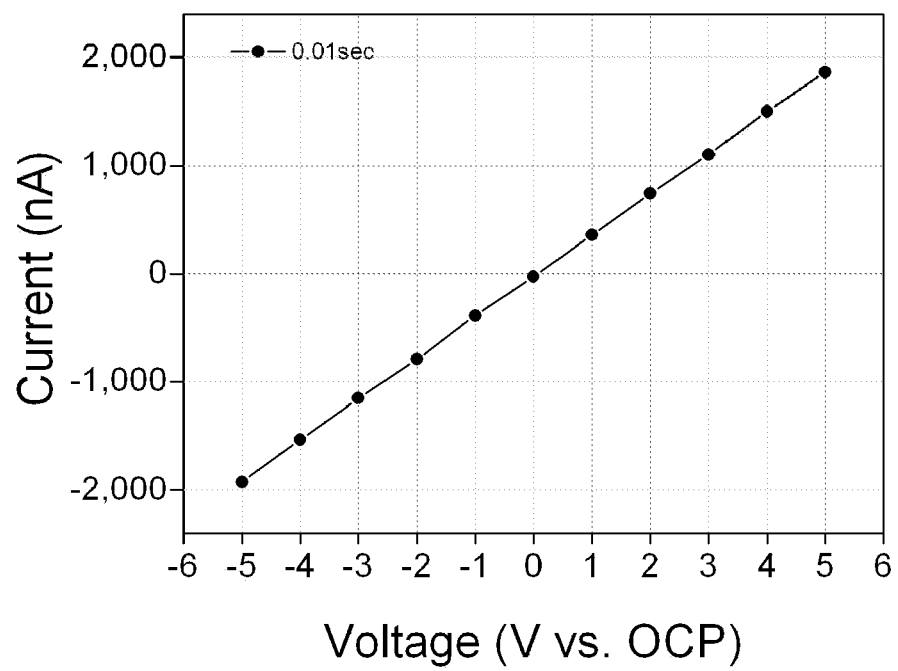
Figure 5C:
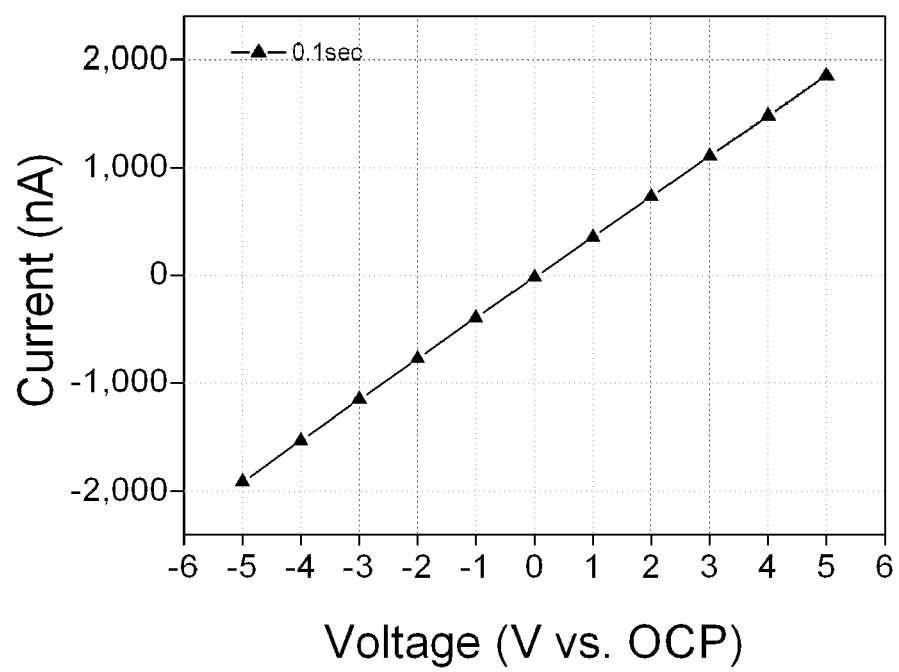
Figure 5D:
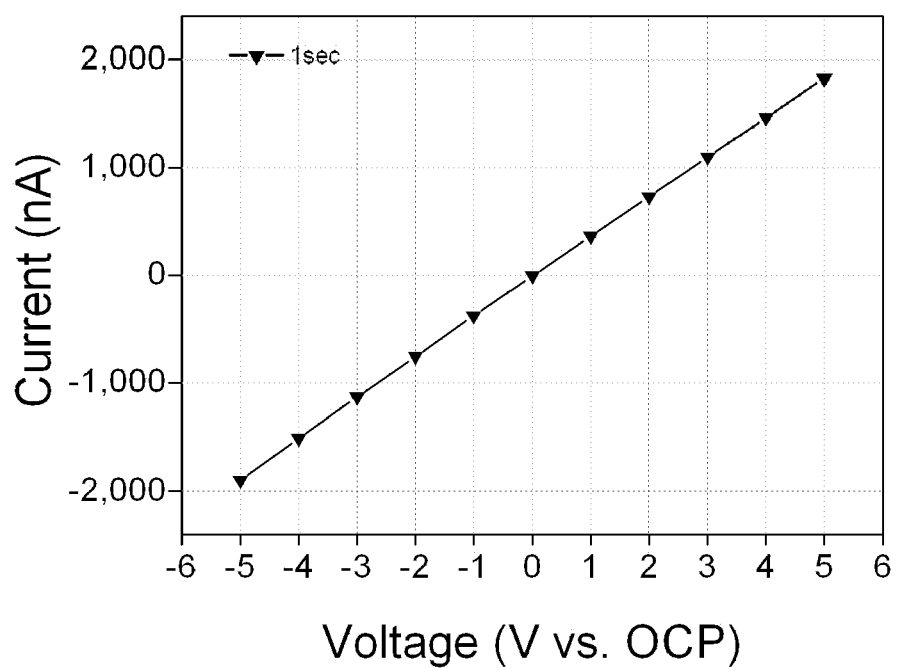
Figure 5E:
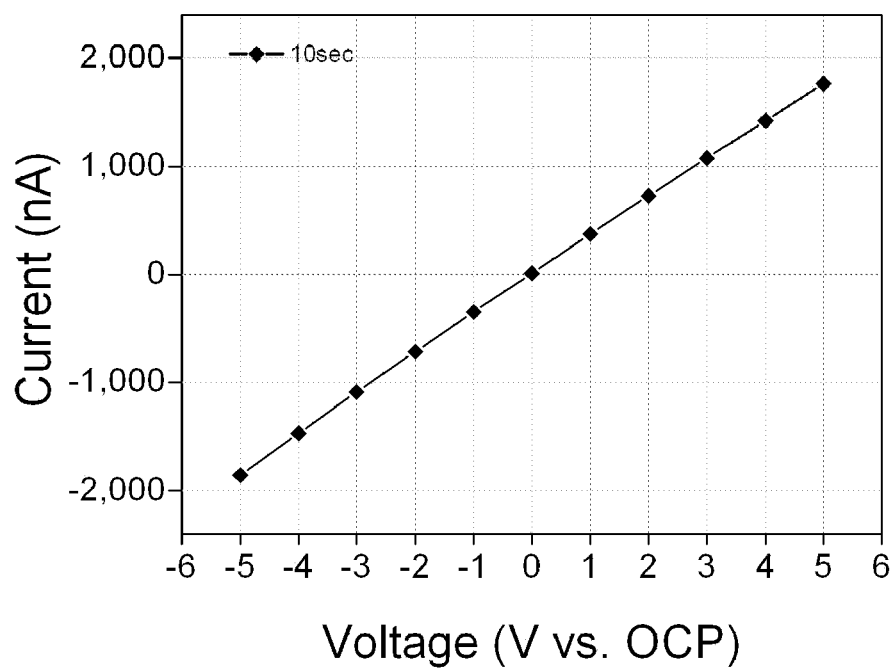
Figure 5F:
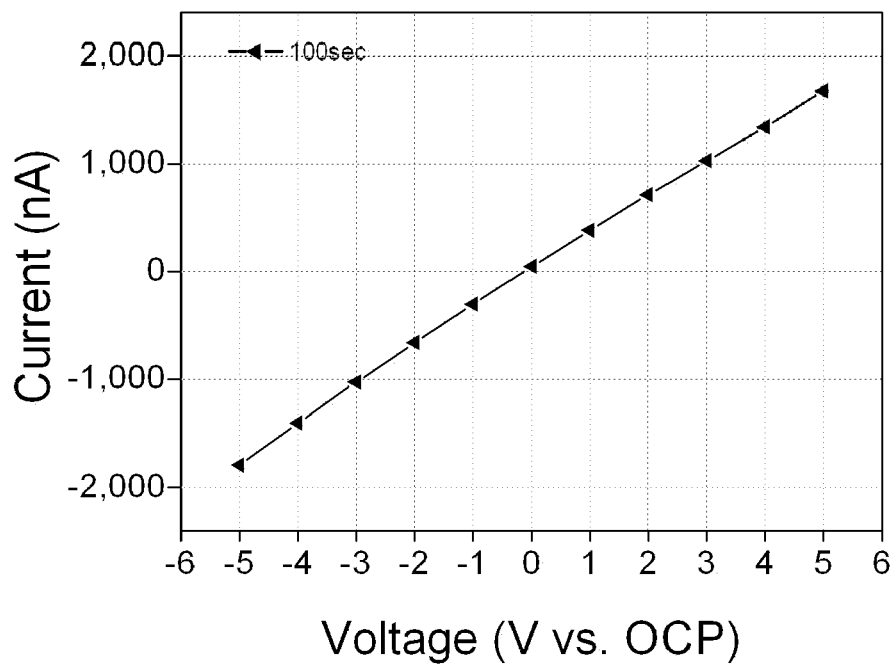
Figure 6A:
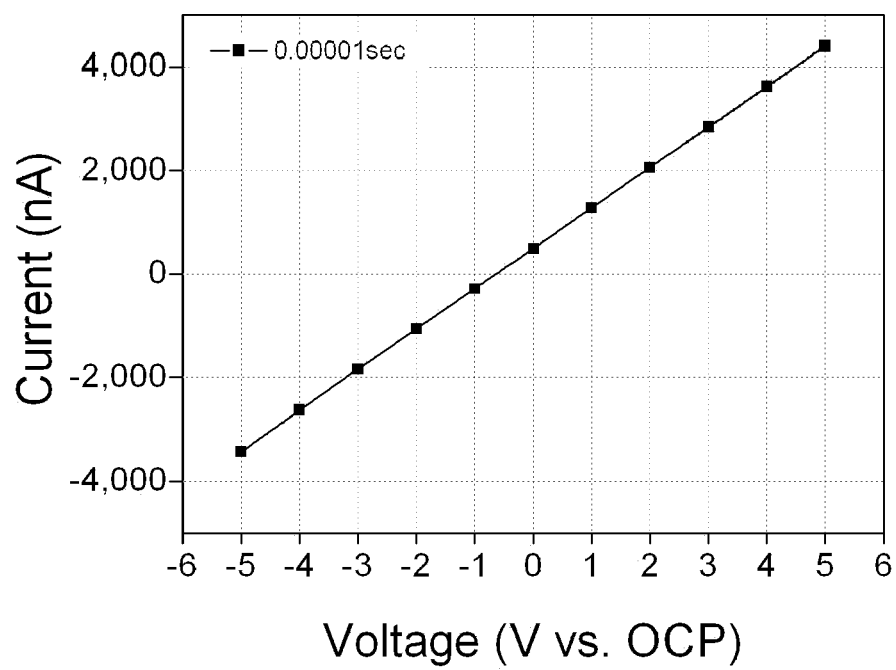
FIGS. 6A to 6G are graphs each illustrating applied voltages and resulting currents in 3M of KCl conductivity standard solution based on a voltage application time.
Figure 6B:
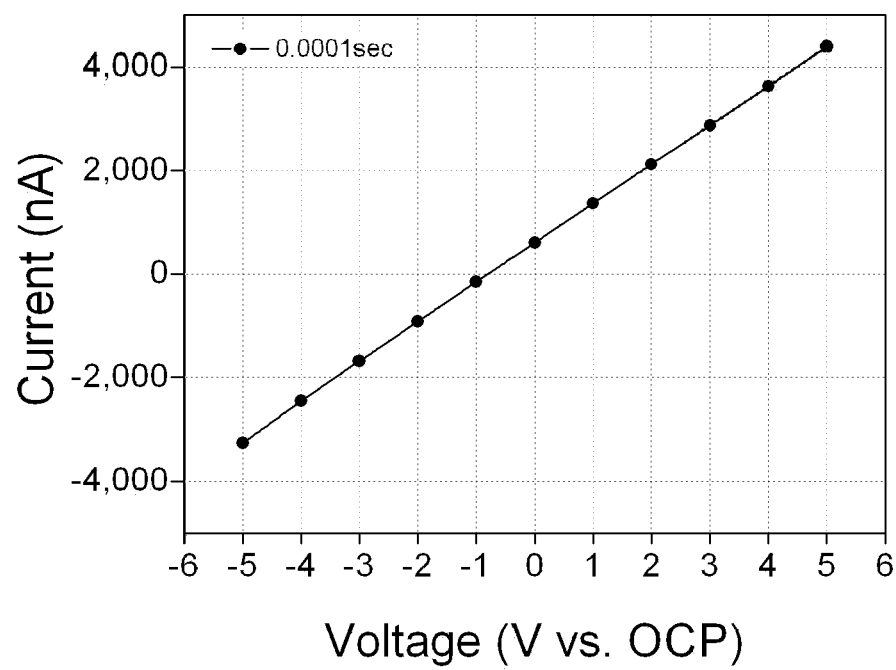
Figure 6C:
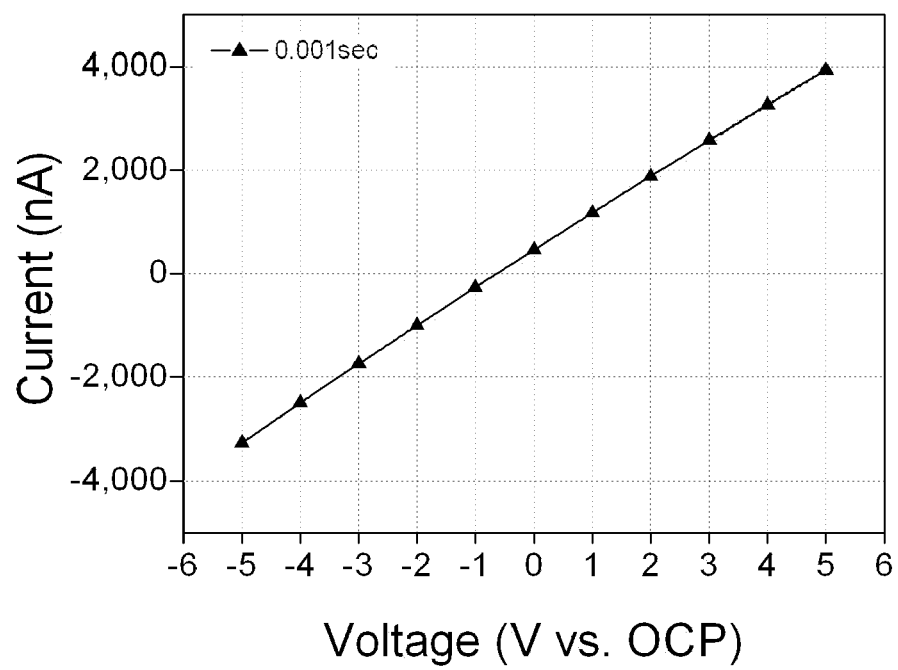
Figure 6D:
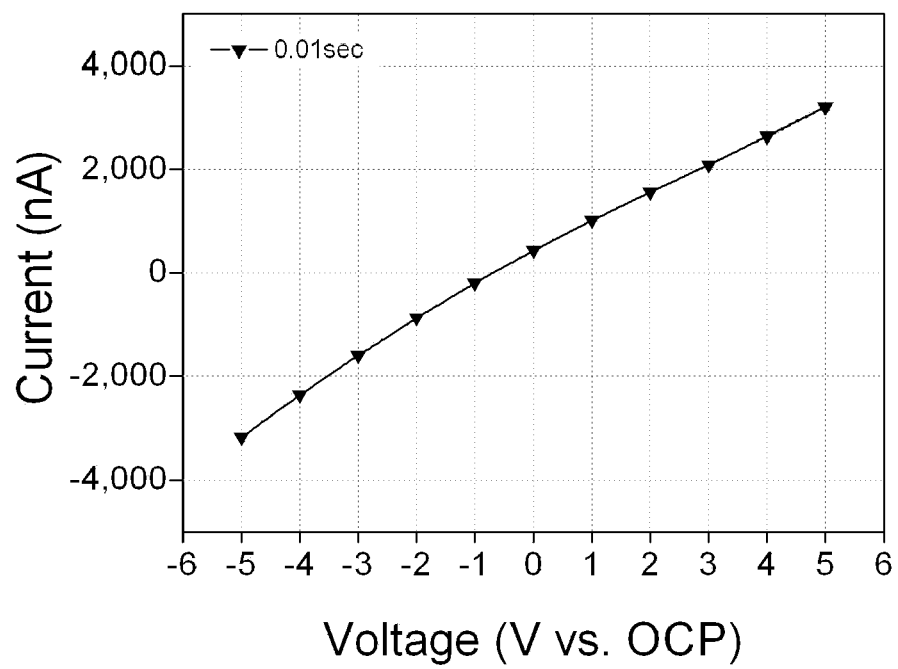
Figure 6E:
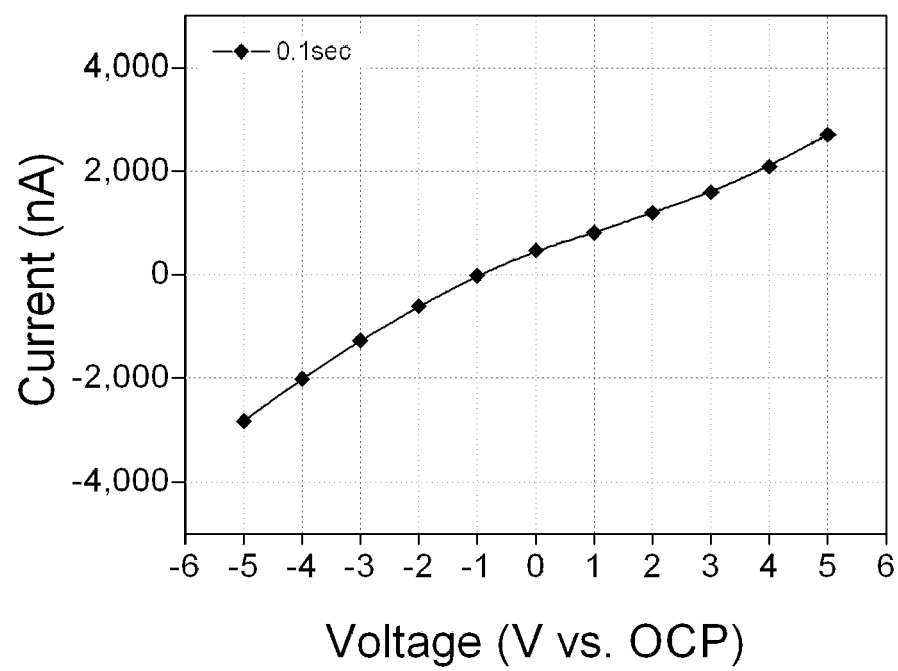
Figure 6F:
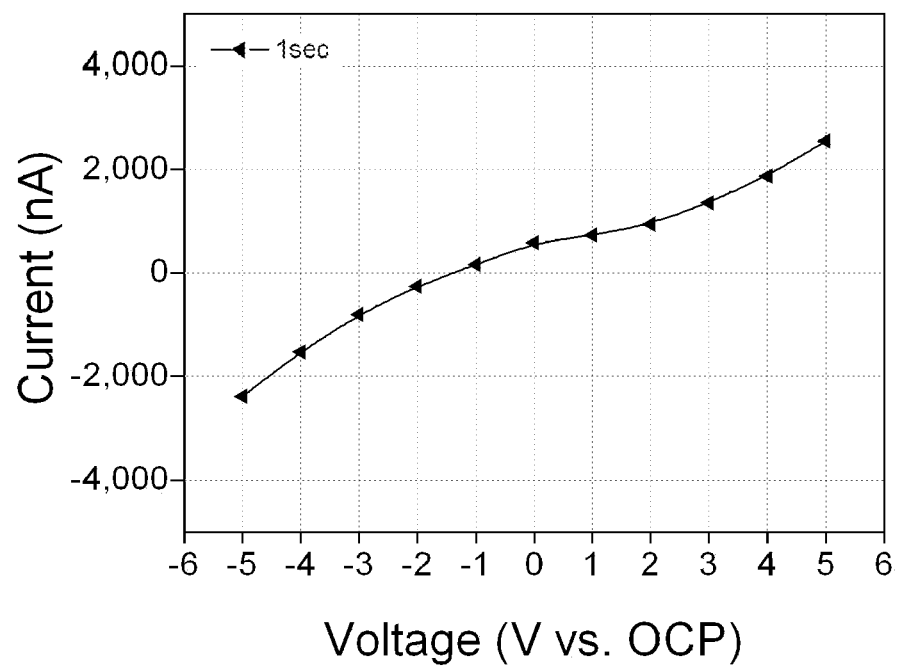
Figure 6G:
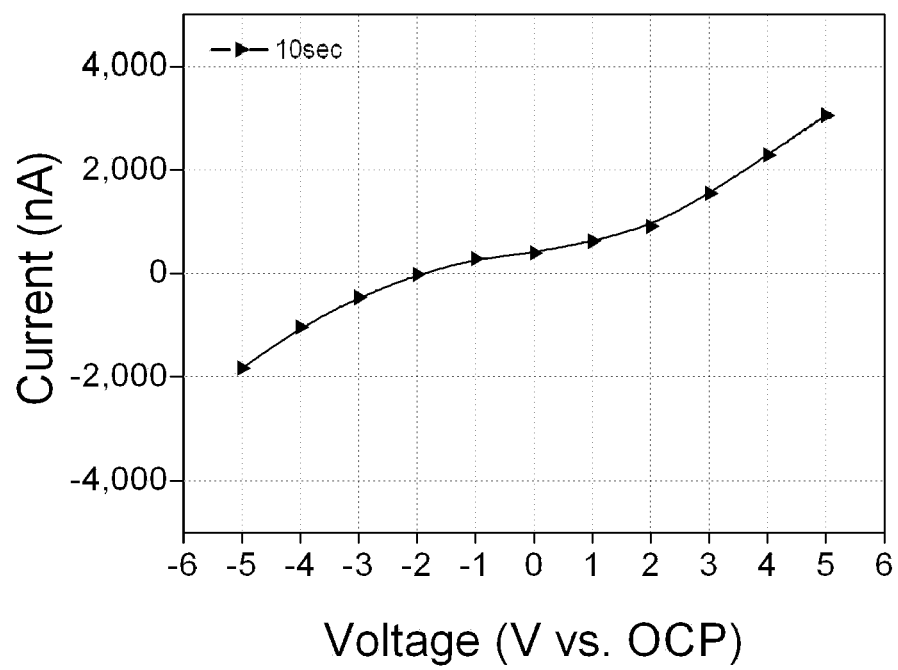

FIG. 4 is a conceptual view illustrating one exemplary embodiment of a system for measuring electrical conductivity in accordance with the present disclosure.

The current measuring unit 130 may measure peak currents for the respective voltages. Since a maximum current (peak current) is recorded at the moment when a voltage is applied, the current measuring unit 130 may read a current value at the moment when the voltage applying unit 130 applies a voltage.

The controller 140 may calculate resistance of the solution 10, as a slope, from a linear relationship between the voltage and the peak current, and then measure the electrical conductivity of the solution 10 using the cell constant and the resistance of the solution 10.

Meanwhile, FIG. 4 merely exemplarily illustrates one embodiment of the electrical conductivity measuring system 100, but the present disclosure may not be limited to the configuration. The electrical conductivity measuring system 100 may be variously varied within the scope to be understood by a skilled person in the art.

Hereinafter, description will be given in more detail of first to fourth exemplary embodiments of the present disclosure.

For reference, a conductance cell used in each embodiment is different from that used in a different exemplary embodiment. Therefore, a cell constant may be different in each embodiment. Here, since the first and second embodiments use the same conductance cell, so as to have the same cell constant.

First Exemplary Embodiment

Measurement of Cell Constant of Conductance Cell in 0.001M of KCl Conductivity Standard Solution This embodiment exemplarily illustrates measurement of a cell constant of a conductance cell. First, after putting 0.001M of KCl conductivity standard solution, which exhibited 127.3 (μS/cm) at 18° C., and electrodes in a conductance cell, voltages from −5V to 5V were applied to the electrodes, each for 0.001 second with an interval of 1V, thereby obtaining currents measured at the respective voltages. Afterwards, those values were diagrammed to obtain a linear slope.

| | Voltage (V) | | | | | | | | | | |
|---|---|---|---|---|---|---|---|---|---|---|---|
| | −5 | −4 | −3 | −2 | −1 | 0 | 1 | 2 | 3 | 4 | 5 |
| Current (nA) | −960 | −773 | −586 | −380 | −184 | −4 | 199 | 401 | 584 | 777 | 984 |

As illustrated in FIG. 4, an electrical conductivity measuring system 100 may include a conductance cell 110, a voltage applying unit 120, a current measuring unit 130 and a controller 140.

The conductance cell 110 may be provided with electrodes 111, and have a specific cell constant. Here, the cell constant is a unique constant of the conductance cell 110, which is decided by a surface area A of the electrode 111 and a distance L between the electrodes 111. The cell constant may be obtained by using the conductivity standard solution, as aforementioned.

The voltage applying unit 120 may apply predetermined DC voltages to the electrodes 111 in a manner of changing the voltages step by step at each preset time. The voltage applying unit 120 may preferably be configured to gradually increase or decrease the voltages at each time, which is shorter than a time that the polarization begins to occur on the surface of the electrode 111.

Since the resistance in the 0.001M of KCl conductivity standard solution is 1/slope (the slope is a current variation according to a voltage variation), if the value of the slope [194.34 (nA/V)] is calculated using the measured value, the resistance of the solution [$5.15 \times 10^6$ (Ω)] may be obtained.

A cell constant may be calculated using the measured resistance, which may be expressed by Equation 1 as follows.

Cell constant=Electrical conductivity×Resistance of solution     (Equation 1)

When the resistance value of the solution and the already known electrical conductivity value are substituted into Equation 1, the cell constant may be decided as follows.

Cell constant=127.3 (μS/cm)×$5.15 \times 10^6$ (Ω)=656 (cm$^{-1}$)

Second Exemplary Embodiment

Measurement of Electrical Conductivity of 0.1M of KCl Conductivity Standard Solution The second exemplary embodiment illustrates a process of measuring electrical conductivity of 0.1M of KCl conductivity standard solution using the cell constant of the conductance cell, obtained in the first exemplary embodiment. First, in order to measure resistance in 0.1M of KCl conductivity standard solution, 0.1M of KCl conductivity standard solution was poured into a conductance cell, and thereafter voltages from −5V to 5V were applied to the electrodes, each for 0.0001 second with an interval of 1V, thereby obtaining currents measured at the respective voltages.

| | Voltage (V) | | | | | | | | | | |
|---|---|---|---|---|---|---|---|---|---|---|---|
| | −5 | −4 | −3 | −2 | −1 | 0 | 1 | 2 | 3 | 4 | 5 |
| Current (nA) | −79.5 | −62.6 | −44.6 | −28.3 | −10.4 | 6.4 | 23.0 | 40.5 | 56.9 | 74.3 | 91.1 |

A value of a slope, which is a current variation according to a voltage variation, is obtained as 17.052 (μA/V) using the measured values, and the 0.1M KCl conductivity standard solution has a resistance value of $5.8644 \times 10^4$ (Ω). The electrical conductivity of the 0.1M KCl conductivity standard solution may be obtained by dividing the cell constant by the resistance value based on the relationship of the previous Equation 1.

Electrical conductivity of 0.1M KCl conductivity standard solution=Cell constant/Resistance of 0.1M KCl conductivity standard solution=656 (cm$^{-1}$)/5.8644×10$^4$ (Ω)=11,186 (μS/cm)

The calculation result shows that upon comparing with the electrical conductivity value known as 11,167 (μS/cm) at 18° C., the electrical conductivity of the 0.1M KCl conductivity standard solution is equal to the known electrical conductivity within an error range of 0.2%.

Third Exemplary Embodiment

Measurement of Electrical Conductivity According to Voltage Application Time This exemplary embodiment illustrates that a more accurate value can be obtained when a shorter voltage application time is set, upon deciding a cell constant of a conductance cell or measuring resistance of a solution using the conductance cell. That is, the voltage application time may preferable be as short as polarization not occurring on the electrode. As can be noticed from the experimental results, a more accurate value may be obtained as the voltage application time is more converged on 0.

On the other hand, a current has to be measured within a voltage application time. Hence, the current measurement time should also be short, similar to the voltage application time.

This exemplary embodiment illustrates that a voltage application time may be differently set depending on a concentration of a solution and simultaneously a voltage application time for a solution with high concentration is preferably shorter than that for a solution with low concentration because the polarization, occurred on the electrode in response to a voltage applied, occurs differently in 0.001M KCl conductivity standard solution with low concentration and 3M KCl conductivity standard solution with high concentration.

In the 0.001M KCl conductivity standard solution with the low concentration, after calculating a linear slope by setting each voltage application time to 0.001 second, 0.01 second, 0.1 second, 1 second, 10 seconds, and 100 seconds, and diagramming changes of currents in response to the changes of voltages, as illustrated in FIGS. 5A to 5F, the cell constants were obtained as follows. According to the results, it can be noticed that the cell constants are converged when the voltage application time is below 0.1 second.

| | Set time (Sec) | | | | | |
|---|---|---|---|---|---|---|
| | 0.001 | 0.01 | 0.1 | 1 | 10 | 100 |
| Cell constant (cm$^{-1}$) | 334 | 336 | 338 | 342 | 352 | 369 |

In the 3M KCl conductivity standard solution with the high concentration, each voltage application time was set to 0.00001 second, 0.0001 second, 0.001 second, 0.01 second, 0.1 second, 1 second and 10 second, and changes of currents in response to the changes of the voltages were diagrammed as illustrated in FIGS. 6A to 6G. According to the results, it can be noticed that cell constants in the 3M KCl conductivity standard solution with the high concentration are converged on a value similar to a cell constant in the 0.001M KCl conductivity standard solution with the low concentration, when the voltage application time is shorter than 0.00001 second. Therefore, it may be appropriate that the voltage application time is set to be less than 0.00001 second.

| | Set time (Sec) | | | | | | |
|---|---|---|---|---|---|---|---|
| | 0.00001 | 0.0001 | 0.001 | 0.01 | 0.1 | 1 | 10 |
| Cell constant (cm$^{-1}$) | 338 | 341 | 350 | 370 | 426 | 513 | 637 |

As such, the voltage application time (T or t) may preferably be longer than 0 second and shorter than or equal to 0.1 second. Of course, as can be observed from the experimental results, the voltage application time may change according to the concentration. That is, the voltage application time for a solution with high concentration may preferably be shorter than that for a solution with low concentration.

Meanwhile, according to the experimental results, the voltage application time was able to be reduced down to 0.0000033 second (namely, 3.3 μs) using currently used equipment. It may be expected that the voltage application time may further be reduced with the technical development of equipment, and more accurate electrical conductivity may be obtained when the voltage application time is shorter.

Fourth Exemplary Embodiment

Dependence on Range of Measurement Voltage and the Number of Measurement Data

This exemplary embodiment illustrates that a voltage range, which is capable of being used in the electrical conductivity measuring system for measurement of the electrical conductivity is unlimited and the step-by-step change of voltages is not limited to a preset number of stages and the shape of each step.

Under conditions that only one conductance cell was used and a voltage application time was set to 0.0001 second, resistances and cell constants, which were measured with respect to 3M KCl conductivity standard solution, were compared.

Figure 7A:
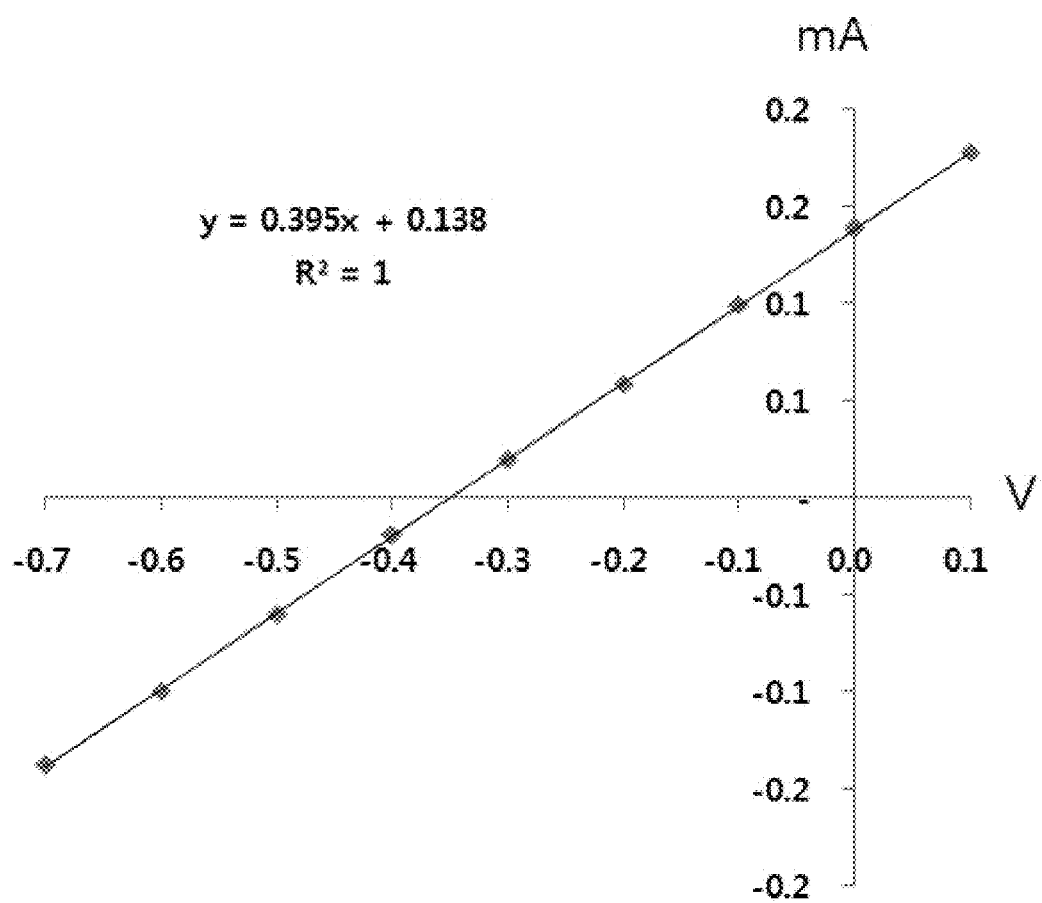
FIGS. 7A to 7C are graphs each illustrating measurement results obtained by changing voltages in stages within a measurement range of voltages applied to 3M KCl conductivity standard solution.
Figure 7B:
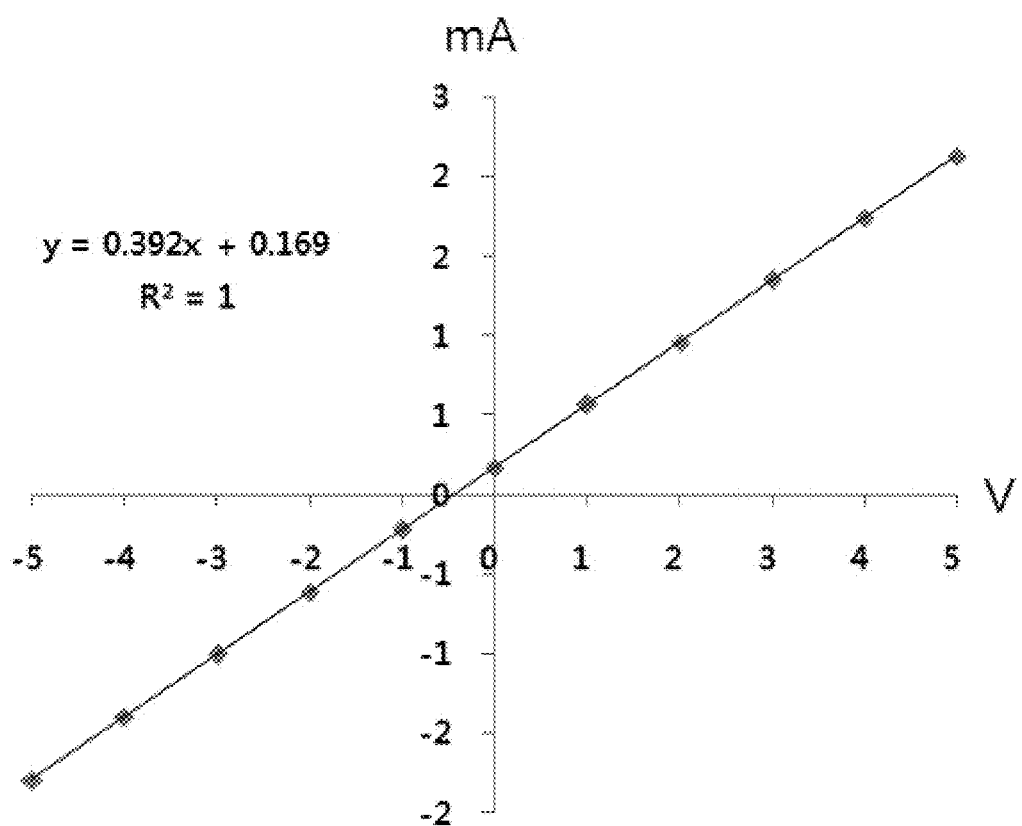
Figure 7C:
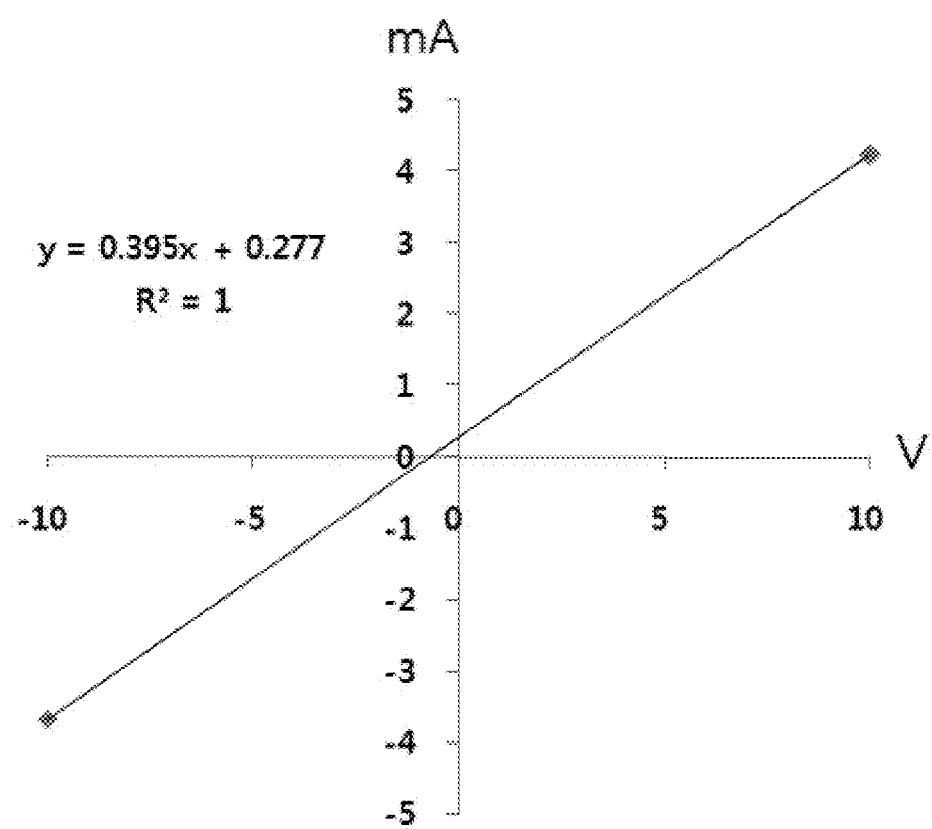

Measurement ranges of applied voltages were between −0.7V and 0.1V, between −5V and 5V, and between −10V and 10, respectively, and the number of stages of changing the voltages was 9 stages, 11 stages and 2 stages, respectively, which were illustrated in FIGS. 7A to 7C. And, each measured resistance and cell constant were diagrammed as follows. It can be understood from the diagrammed results that the voltage can be appropriately increasing at least from the $2^{nd}$ stage.

| Measured voltage | Change step | Resistance of solution (Ω) | Cell constant (cm$^{-1}$) | Remark |
|---|---|---|---|---|
| −0.7 V~0.1 V | 9 | 2,525 | 674 | FIG. 7A |
| −5 V~5 V | 11 | 2,548 | 679 | FIG. 7B |
| −10 V~10 V | 2 | 2,531 | 675 | FIG. 7C |

As described above, according to the present disclosure, by changing predetermined DC voltages in stages at each preset time and measuring resistance of a solution using a peak current measured at each voltage, a measurement error caused due to polarization may be minimized and dependence on electrical conductivity (so-called Parker effect) of a cell constant may be removed, thereby measuring more accurate electrical conductivity of the solution.

The present disclosure may be widely applied to a technical field related to electrochemical systems and the understanding of an ionic structure within a solution, as well as an industrial field, such as water-quality monitoring in an environmental industry, monitoring of cooling water in a nuclear industry, and the like.

The foregoing embodiments and advantages of the method and system for measuring electrical conductivity are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

The invention claimed is:

1. A method for measuring electrical conductivity comprising:
    obtaining a cell constant of a conductance cell using a conductivity standard solution;
    pouring a solution desired to be measured in the conductance cell, and applying predetermined direct current (DC) voltages to electrodes, disposed in the conductance cell, in a manner of changing the predetermined DC voltages in stages at each preset time (t);
    obtaining resistance of the solution, as a slope, from a linear relationship between the voltage and a peak current, the peak current being measured for each voltage; and
    calculating electrical conductivity of the solution using the cell constant and the resistance of the solution.

2. The method of claim 1, wherein the applying by changing the voltages in stages is a step of applying the voltages by increasing or decreasing the voltages in stages at each preset time.

3. The method of claim 1, wherein the preset time is shorter than a time at which polarization begins to occur on a surface of the electrode.

4. The method of claim 3, wherein the preset time is a time converged on 0 (t→0) to prevent the polarization on the surface of the electrode.

5. The method of claim 1, wherein the peak current is a current measured at the moment when the predetermined DC voltage is applied.

6. The method of claim 1, wherein the obtaining of the cell constant comprises:
    applying the predetermined DC voltages to the electrodes by changing the voltages in stages at each preset time (T); and
    obtaining the resistance of the conductivity standard solution, as the slope, from the linear relationship between the voltage and the peak current measured for each voltage.

7. The method of claim 6, wherein the applying by changing the voltages in stages, in the step of obtaining the cell constant, is a step of applying the voltages by increasing or decreasing the voltages in stages at each preset time.

8. The method of claim 6, wherein the preset time is shorter than a time at which polarization begins to occur on a surface of the electrode.

9. The method of claim 8, wherein the preset time is a time converged on 0 (T→0) to prevent the polarization on the surface of the electrode.

10. A system for measuring electrical conductivity comprising:
    a conductance cell having electrodes, the conductance cell having an unique cell constant;
    a voltage applying unit that is configured to apply predetermined direct current (DC) voltages to the electrodes by changing the voltages in stages at each preset time;
    a current measuring unit that is configured to measure a peak current for each voltage; and
    a controller that is configured to obtain resistance of the solution, as a slope, from a linear relationship between the voltage and the peak current, and calculate electrical conductivity of the solution using the cell constant and the resistance of the solution.

11. The system of claim 10, wherein the voltage applying unit is configured to increase or decrease the voltages in stages at each time, which is shorter than a time when polarization begins to occur on a surface of the electrode.

12. The system of claim 10, wherein the current measuring unit is configured to measure a current at the moment when the predetermined DC voltage is applied.

* * * * *